(12) United States Patent
Sakurai

(10) Patent No.: US 11,654,209 B2
(45) Date of Patent: May 23, 2023

(54) BOARDING HANDRAIL DISINFECTING DEVICE

(71) Applicant: TOYOTA JIDOSHA KABUSHIKI KAISHA, Aichi-ken (JP)

(72) Inventor: Hideyuki Sakurai, Toyota (JP)

(73) Assignee: TOYOTA JIDOSHA KABUSHIKI KAISHA, Aichi-ken (JP)

( * ) Notice: Subject to any disclaimer, the term of this patent is extended or adjusted under 35 U.S.C. 154(b) by 190 days.

(21) Appl. No.: 17/367,426

(22) Filed: Jul. 5, 2021

(65) Prior Publication Data

US 2022/0062471 A1  Mar. 3, 2022

(30) Foreign Application Priority Data

Aug. 31, 2020 (JP) .............................. JP2020-146329

(51) Int. Cl.
*A61L 2/10* (2006.01)
*A61L 2/26* (2006.01)

(52) U.S. Cl.
CPC .................. *A61L 2/10* (2013.01); *A61L 2/26* (2013.01); *A61L 2202/11* (2013.01)

(58) Field of Classification Search
CPC ..... A61L 2/10; A61L 2/24; A61L 2/26; A61L 2/0047; A61L 9/20; A61L 2202/11; A61L 2202/14; A61L 2202/16; A61L 2209/12; A61L 2209/15; A61L 2209/111
See application file for complete search history.

(56) References Cited

U.S. PATENT DOCUMENTS

| 3,344,959 | A | * | 10/1967 | Faso | B65D 83/267 222/394 |
| 3,994,440 | A | * | 11/1976 | Mancini | B65D 83/267 239/274 |
| 4,046,508 | A | * | 9/1977 | McDonald | A61L 2/18 4/222 |
| 4,710,634 | A | * | 12/1987 | Brookes | E05B 1/0069 16/904 |
| 5,314,668 | A | * | 5/1994 | Biermaier | A61L 2/18 422/301 |
| 7,080,427 | B1 | * | 7/2006 | Campopiano | E05B 1/0069 422/301 |
| 7,175,807 | B1 | * | 2/2007 | Jones | E05B 1/0069 250/493.1 |
| 7,338,646 | B2 | * | 3/2008 | Gilbert | E05B 1/0069 422/292 |
| 7,850,114 | B2 | * | 12/2010 | Lavy | A47K 10/46 16/904 |

(Continued)

FOREIGN PATENT DOCUMENTS

JP          202063050 A    4/2020

*Primary Examiner* — Sean M Luck
(74) *Attorney, Agent, or Firm* — Hauptman Ham, LLP

(57) ABSTRACT

A boarding handrail disinfecting device includes: a cover member that is provided on a door for opening and closing an entrance of a vehicle, and that is disposed so as to closely face a boarding handrail provided on a periphery of the entrance when the door closes the entrance and withdrawn from the boarding handrail when the door opens the entrance; and an irradiation device that is provided on a surface of the cover member that faces the boarding handrail and irradiates the boarding handrail with ultraviolet light.

4 Claims, 15 Drawing Sheets

(56) References Cited

U.S. PATENT DOCUMENTS

| | | | | |
|---|---|---|---|---|
| 7,989,779 | B1* | 8/2011 | Ray | A61L 2/10 250/493.1 |
| 8,658,106 | B2* | 2/2014 | Van Zijl | A61L 2/22 422/107 |
| 9,649,398 | B1* | 5/2017 | York | E05B 1/0069 |
| 9,896,865 | B2* | 2/2018 | Samaras | E05B 1/0069 |
| 10,455,936 | B2* | 10/2019 | McKnight | G08B 21/245 |
| 10,487,537 | B2* | 11/2019 | Cunningham | B08B 3/02 |
| 11,077,218 | B1* | 8/2021 | Gagnon | G07F 7/005 |
| 2005/0011042 | A1* | 1/2005 | Hupp | E05B 1/0069 16/110.1 |
| 2006/0076743 | A1* | 4/2006 | Dunser | B62B 3/14 280/33.992 |
| 2009/0193607 | A1* | 8/2009 | Adell | B08B 1/008 15/246 |
| 2011/0174992 | A1* | 7/2011 | Sakita | A61L 2/10 250/492.1 |
| 2012/0131756 | A1* | 5/2012 | Gilsenan | A61L 2/18 15/103.5 |
| 2012/0176241 | A1* | 7/2012 | Pasch | A61L 2/24 250/492.1 |
| 2012/0305804 | A1* | 12/2012 | Goldman | E05B 1/0069 250/492.1 |
| 2013/0240756 | A1* | 9/2013 | Segal | A61L 2/10 250/492.1 |
| 2014/0048724 | A1* | 2/2014 | Marshall | A61L 2/10 250/492.1 |
| 2014/0208541 | A1* | 7/2014 | Cowburn | E05B 1/0069 16/110.1 |
| 2014/0322073 | A1* | 10/2014 | Link | A61L 2/10 250/492.1 |
| 2016/0249436 | A1* | 8/2016 | Inskeep | A61L 2/10 |
| 2017/0165387 | A1* | 6/2017 | Robert | A61L 9/22 |
| 2017/0246332 | A1* | 8/2017 | Marshall | E05B 1/0069 |
| 2017/0252550 | A1* | 9/2017 | Wegener | F16K 7/045 |
| 2017/0333580 | A1* | 11/2017 | Cahan | A61L 2/26 |
| 2018/0339075 | A1* | 11/2018 | Kennedy | A61L 2/24 |
| 2019/0269810 | A1* | 9/2019 | Brehm | A61M 1/14 |
| 2021/0047860 | A1* | 2/2021 | Grau | E05B 1/0015 |
| 2022/0062471 | A1* | 3/2022 | Sakurai | B60N 3/023 |

\* cited by examiner

BOARDING HANDRAIL DISINFECTING DEVICE

CROSS-REFERENCE TO RELATED APPLICATION

This application claims priority to Japanese Patent Application No. 2020-146329 filed on Aug. 31, 2020, incorporated herein by reference in its entirety.

BACKGROUND

1. Technical Field

The present disclosure relates to a boarding handrail disinfecting device.

2. Description of Related Art

There is a hitherto known hanging strap disinfecting device (e.g., see Japanese Unexamined Patent Application Publication No. 2020-063050). This device includes a light-blocking cover that is provided over an upper part of a handle of a hanging strap, and light emitting elements that are provided inside the cover and capable of emitting ultraviolet light, and disinfects the handle, which is rotatable in a circumferential direction, by irradiating the upper part of the handle covered by the cover with ultraviolet light.

SUMMARY

In the case of a hanging strap, since a passenger grasps the hanging strap by reaching out his or her hand from below, a disinfecting device permanently equipped with a cover as described above also works. In the case of a boarding handrail provided on a periphery of an entrance of a bus etc., however, passengers grasp the boarding handrail from various directions. Thus, a disinfecting device including a cover as described above that is permanently installed on the boarding handrail would make the boarding handrail difficult to grasp and hinder its original function as a boarding handrail.

It is therefore an object of the present disclosure to obtain a boarding handrail disinfecting device that can disinfect a boarding handrail without hindering it from functioning as a boarding handrail.

To achieve this object, a boarding handrail disinfecting device described in one aspect of the present disclosure includes: a cover member that is provided on a door for opening and closing an entrance of a vehicle, and that is disposed so as to closely face a boarding handrail provided on a periphery of the entrance when the door closes the entrance and withdrawn from the boarding handrail when the door opens the entrance; and an irradiation device that is provided on a surface of the cover member that faces the boarding handrail and irradiates the boarding handrail with ultraviolet light.

With the above aspect, the cover member is disposed so as to closely face the boarding handrail provided on the periphery of the entrance of the vehicle when the door for opening and closing the entrance closes the entrance, and is withdrawn from the boarding handrail when the door opens the entrance. Therefore, passengers can grasp the boarding handrail from various directions, and the function of a boarding handrail is not hindered. Further, while the door closes the entrance, ultraviolet light is emitted from the irradiation device provided on the surface of the cover member that faces the boarding handrail. Thus, the boarding handrail is sterilized (disinfected).

In the above aspect, the cover member has an extending part that extends and covers the boarding handrail after the door is closed.

With the above configuration, the extending part of the cover member extends and covers the boarding handrail after the door is closed. Thus, a disinfection treatment can be intensively performed while the boarding handrail is not used.

In the above aspect, a reflective member capable of reflecting ultraviolet light is provided on a surface of the extending part that faces the boarding handrail.

With the above configuration, the reflective member capable of reflecting ultraviolet light is provided on the surface of the extending part that faces the boarding handrail. Thus, the boarding handrail can be irradiated with ultraviolet light from various angles.

In the above aspect, wherein a reflective member capable of reflecting ultraviolet light is provided on a part of the door that closely faces the boarding handrail when the door closes the entrance.

With the above configuration, the reflective member capable of reflecting ultraviolet light is provided on a part of the door that closely faces the boarding handrail when the door closes the entrance. Thus, the boarding handrail can be irradiated with ultraviolet light from various angles.

As has been described above, the present disclosure can disinfect a boarding handrail without hindering it from functioning as a boarding handrail.

BRIEF DESCRIPTION OF THE DRAWINGS

Features, advantages, and technical and industrial significance of exemplary embodiments of the disclosure will be described below with reference to the accompanying drawings, in which like numerals denote like elements, and wherein.

DETAILED DESCRIPTION OF EMBODIMENTS

Figure 1:
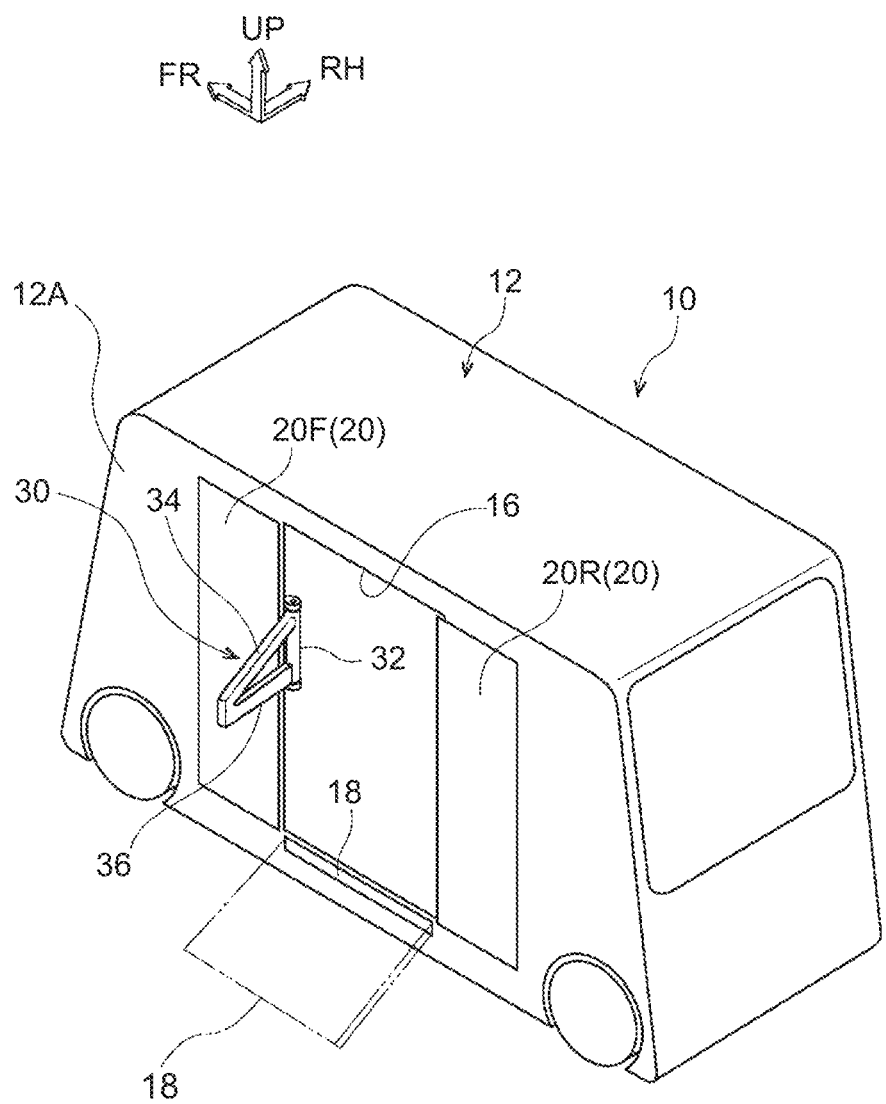
FIG. 1 is a perspective view showing a bus equipped with a boarding handrail disinfecting device according to a first embodiment.

Embodiments according to the present disclosure will be described in detail below based on the drawings. A boarding handrail 30 and a disinfecting device 50 thereof according to the embodiments are suitably provided in a small bus 10 that is one example of passenger-carrying cars as a vehicle (see FIG. 1). (The term "bus" here covers vehicles used for Mobility as a Service (MaaS) represented by a self-driving bus.)

For the convenience of description, arrows UP, FR, LH, and RH shown as necessary in the drawings indicate directions toward a vehicle body upper side, a vehicle body front side, a vehicle body left side, and a vehicle body right side, respectively, of the bus 10. Unless otherwise noted, the directions of up and down, front and rear, and left and right mentioned in the following description mean up and down in a vehicle body up-down direction, front and rear in a vehicle body front-rear direction, and left and right in a vehicle body left-right direction (vehicle width direction).

First Embodiment

First, a first embodiment will be described. As shown in FIG. 1, an entrance 16 having a rectangular shape as seen in a side view is formed in a left side wall (one side wall) of a vehicle body 12 of the bus 10, at a substantially central part in the front-rear direction. The bus 10 is provided with a sliding door 20 as a door that opens and closes the entrance 16.

The sliding door 20 is composed of a front-side door half 20F and a rear-side door half 20R each having a rectangular shape of which the length in the up-down direction is longer than the length in the front-rear direction as seen in a side view. The sliding door 20 is configured to be able to open and close the entrance 16 as the front-side door half 20F and the rear-side door half 20R slide (move) synchronously along an outer wall surface 12A of the bus 10 in directions toward and away from each other.

Elastic bodies 22 (see FIG. 6), such as rubber, are attached to end surfaces of the door halves 20F, 20R on inner sides in the front-rear direction (in other words, a rear end surface of the door half 20F and a front end surface of the door half 20R) that come into contact with each other when closing the entrance 16, along the entire end surfaces in the up-down direction. The door halves 20F, 20R close the entrance 16 by bringing their respective elastic bodies 22 into contact with each other so as to elastically deform.

Figure 7:
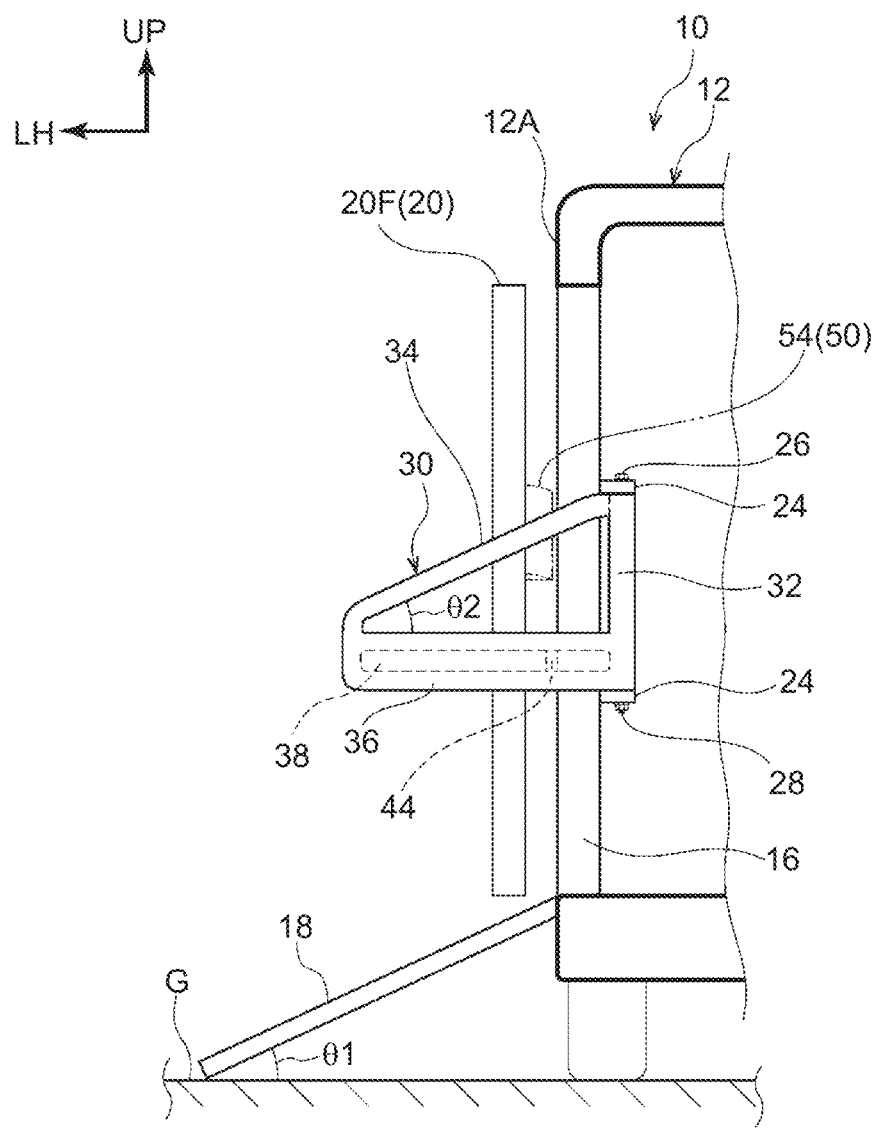
FIG. 7 is a rear view showing a deployed posture of the boarding handrail according to the first embodiment.

As shown in FIG. 1, a slope 18 that can be protruded to the outside of the vehicle is housed in the vehicle body 12, under the entrance 16 (e.g., under a floor panel). The slope 18 has a flat plate shape and is configured to be electrically operated to be pulled out and housed. As shown in FIG. 7, when pulled out, the slope 18 is disposed at a predetermined inclination angle θ1 by having a leading end thereof in a pull-out direction supported on a road surface G.

As shown in FIG. 1, when the sliding door 20 (the door half 20F and the door half 20R) slides (moves) and opens the entrance 16, a boarding handrail 30 made of metal (e.g., aluminum) protrudes from a predetermined position in the entrance 16 in the up-down direction (height direction) toward an outer side in the vehicle width direction.

Figure 2:
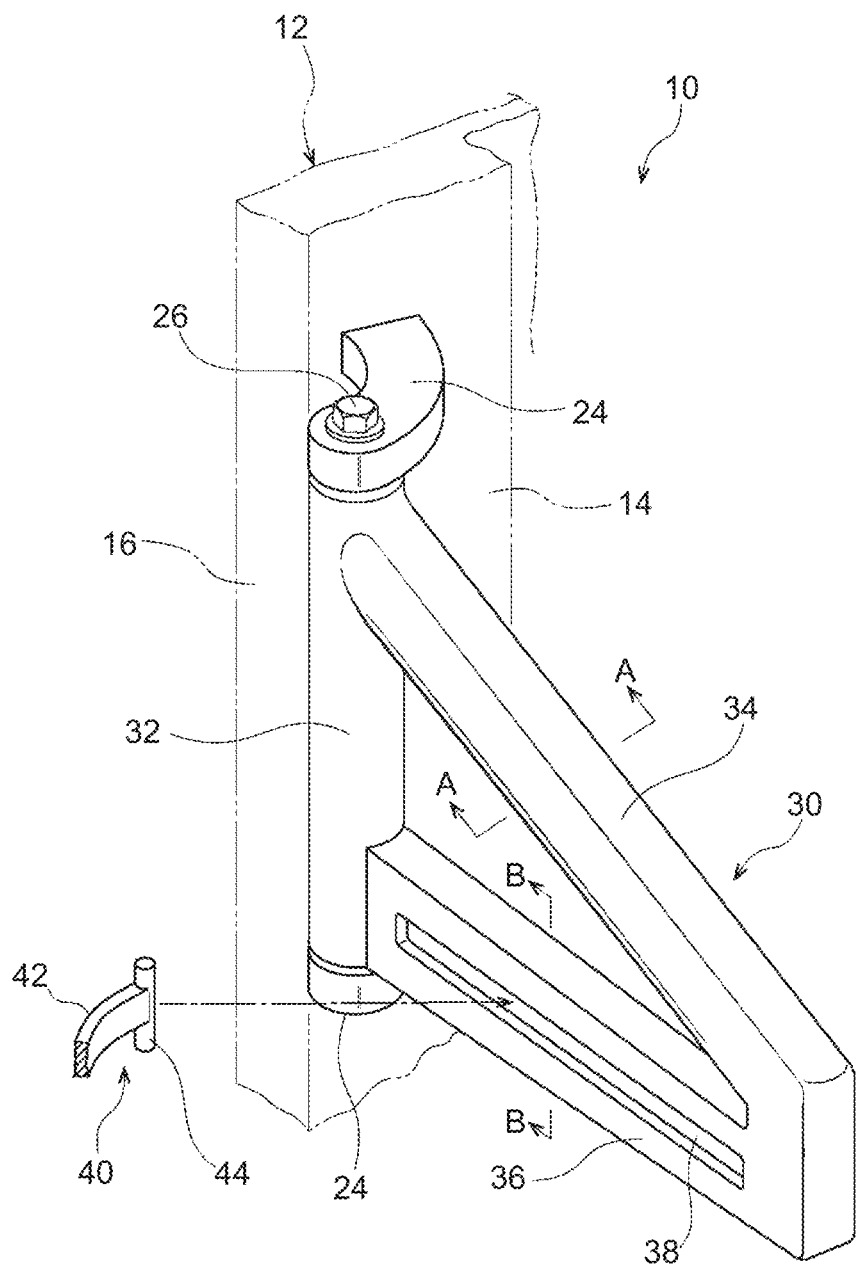
FIG. 2 is a perspective view showing a boarding handrail according to the first embodiment.

Specifically, as shown in FIG. 2, the boarding handrail 30 includes a cylindrical base 32, a handrail main body 34 of which one end is integrally provided at an upper part of an outer peripheral surface of the base 32, and a rail 36 of which one end is integrally provided at a lower part of the outer peripheral surface of the base 32. The other end (a leading end in an extension direction) of the handrail main body 34 and the other end of the rail 36 are integrally joined together.

The base 32 is provided on a periphery of the entrance 16 of the bus 10 (e.g., on an inner wall surface of a pillar 14) so as to be rotatable with an axial direction oriented in the up-down direction. For example, the base 32 is disposed between a pair of upper and lower brackets 24 provided on the inner wall surface of the pillar 14. A shaft of a bolt 26 is inserted from above into through-holes (not shown) formed in the respective brackets 24 and a through-hole (not shown) in the base 32 and screwed onto a nut 28 (see FIG. 5 and FIG. 7), and thus the base 32 is rotatably supported by the brackets 24.

Figure 4A:
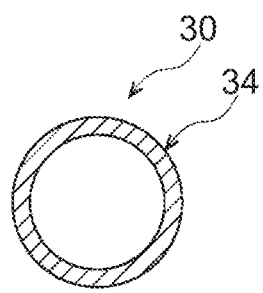
FIG. 4A is a sectional view taken along line A-A of FIG. 2 and seen in the arrow direction.

As shown in FIG. 4A, the handrail main body 34 has a cylindrical shape (a circular shape in cross-section). As shown in FIG. 2 and FIG. 7, the handrail main body 34 extends from the upper part of the base 32 toward an obliquely lower side. Thus, the handrail main body 34 is disposed so as to be inclined relatively to a horizontal direction, and a right-angled triangle is formed by the handrail main body 34, the base 32, and the rail 36. An inclination angle θ2 of the handrail main body 34 relative to the horizontal direction is set to an inclination angle roughly equal to the inclination angle θ1 of the slope 18 (see FIG. 7).

As shown in FIG. 2 and FIG. 7, the rail 36 extends in a horizontal direction and integrally couples a lower part of the base 32 and the other end (the leading end in the extension direction) of the handrail main body 34 together. The rail 36 slidably holds a sliding member 40 (see also FIG. 3) that is mounted at an end of, for example, the door half 20F of the sliding door 20 on the inner side in the front-rear direction.

Figure 4B:
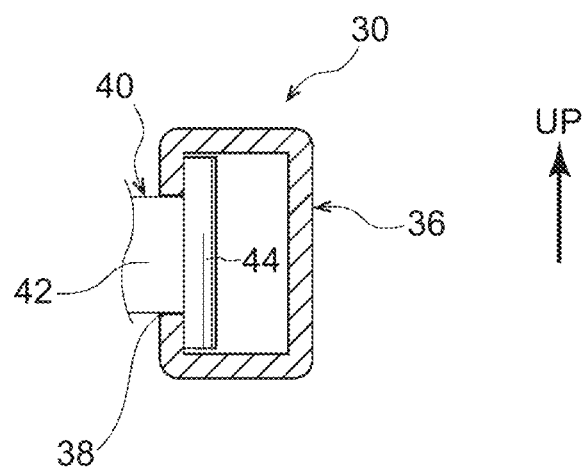
FIG. 4B is a sectional view taken along line B-B of FIG. 2 and seen in the arrow direction, showing a state where the sliding member is held by the rail.

As shown in FIG. 4B, the rail 36 has a rectangular tubular shape (a rectangular shape in cross-section) with the long sides oriented in the up-down direction. As shown in FIG. 2, a slit 38 communicating with the inside of the rail 36 and having a predetermined length along an extension direction (longitudinal direction) thereof is formed in one side wall of the rail 36 (the side wall that faces the front side in a deployed posture to be described later and faces the outer side in the vehicle width direction in a retracted posture to be described later), at a substantially central part in the up-down direction. Since the rail 36 is not to be grasped by passengers, the rail 36 need not have a circular cross-section.

Figure 3:
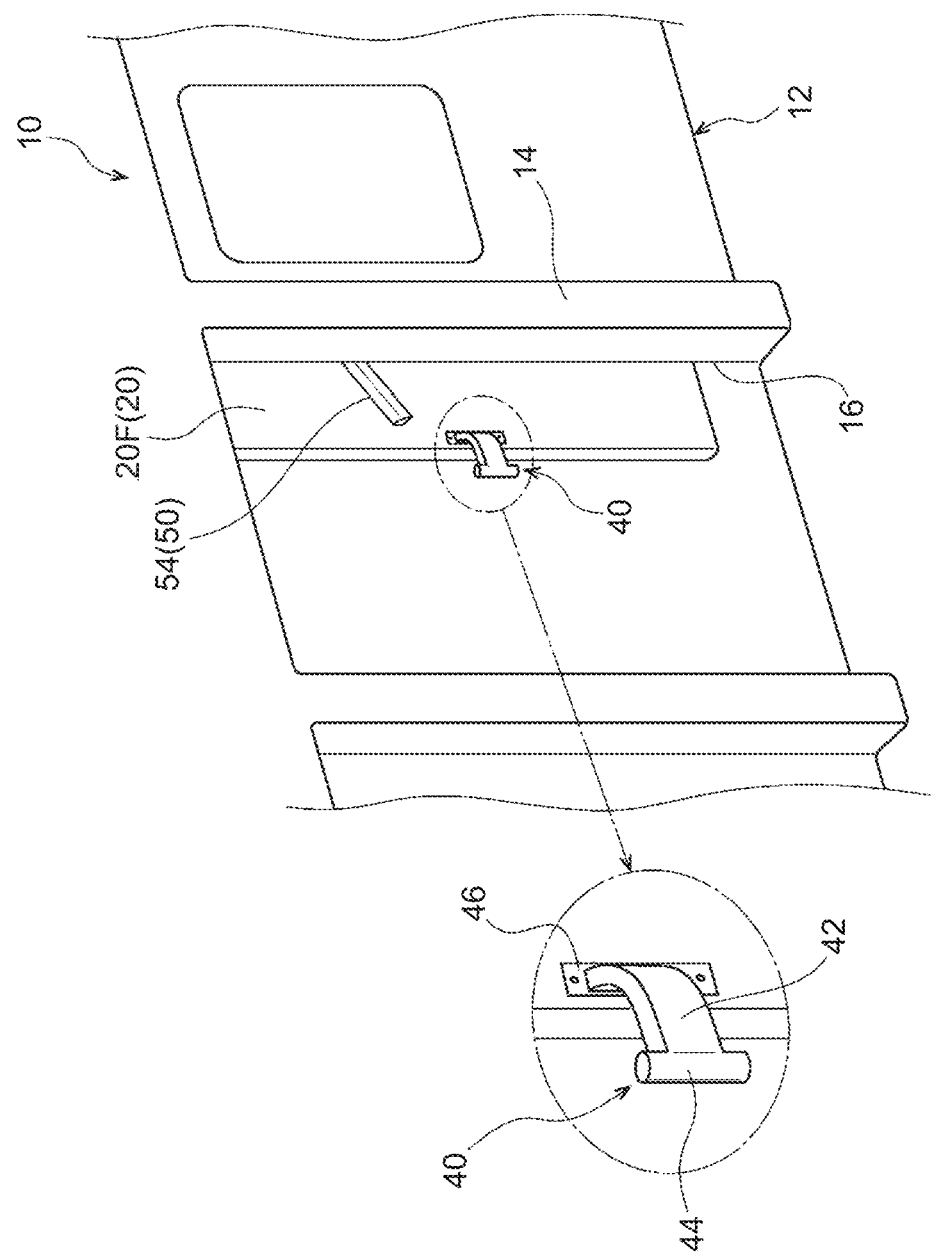
FIG. 3 is a perspective view showing a sliding member that is slidably held by a rail of the boarding handrail according to the first embodiment.

As shown in FIG. 3, the sliding member 40 has a substantially T-shape as seen in a side view. That is, the sliding member 40 has a main body 42 that has a curved plate shape as seen in a plan view, a substantially columnar fitting part 44 that protrudes in the up-down direction from a leading end of the main body 42 (has an axial direction oriented in the up-down direction), and a flat plate-shaped fixing part 46 that is formed at a base end of the main body 42 on the opposite side from the fitting part 44.

The sliding member 40 is mounted to the rail 36 before the fixing part 46 is mounted to the door half 20F. Specifically, the fitting part 44 of the sliding member 40 is held laterally (with the axial direction oriented in a horizontal direction) and passed through the slit 38 of the rail 36 and then turned 90 degrees. Thus, as shown in FIG. 4B, the fitting part 44 of the sliding member 40 is fitted in the rail 36 so as to be slidable in a longitudinal direction of the rail 36, without coming off the rail 36.

Therefore, the width of the slit 38 (the clearance in the up-down direction) is larger than the outside diameter of the fitting part 44 and equal to or slightly larger than the width of the main body 42 of the sliding member 40 (the length of the fitting part 44 along the axial direction as seen in a side view). After the fitting part 44 of the sliding member 40 is fitted in the rail 36, the fixing part 46 thereof is mounted to the end of the door half 20F on the inner side in the front-rear direction by screw fastening or the like. Thus, the rail 36 is supported also by the sliding member 40.

As shown in FIG. 3 and FIG. 5 to FIG. 10, a cover member 54 that is disposed so as to closely face the handrail main body 34 of the boarding handrail 30 from above when the sliding door 20 closes the entrance 16 and withdrawn from the boarding handrail 30 when the sliding door 20 opens the entrance 16 is provided at a predetermined position in the sliding door 20.

In other words, the cover member 54 is disposed so as to closely face the handrail main body 34 from above only when the sliding door 20 closes the entrance 16. The cover member 54 is long enough to extend along the entire handrail main body 34 in a longitudinal direction thereof and has a hollow plate shape with a predetermined thickness. The cover member 54 is integrally mounted on an inner wall surface of the door half 20F that faces the vehicle cabin, at an inclination angle θ2 relative to a horizontal direction, so as to be disposed parallel to the handrail main body 34 having assumed the retracted posture.

Figure 8:
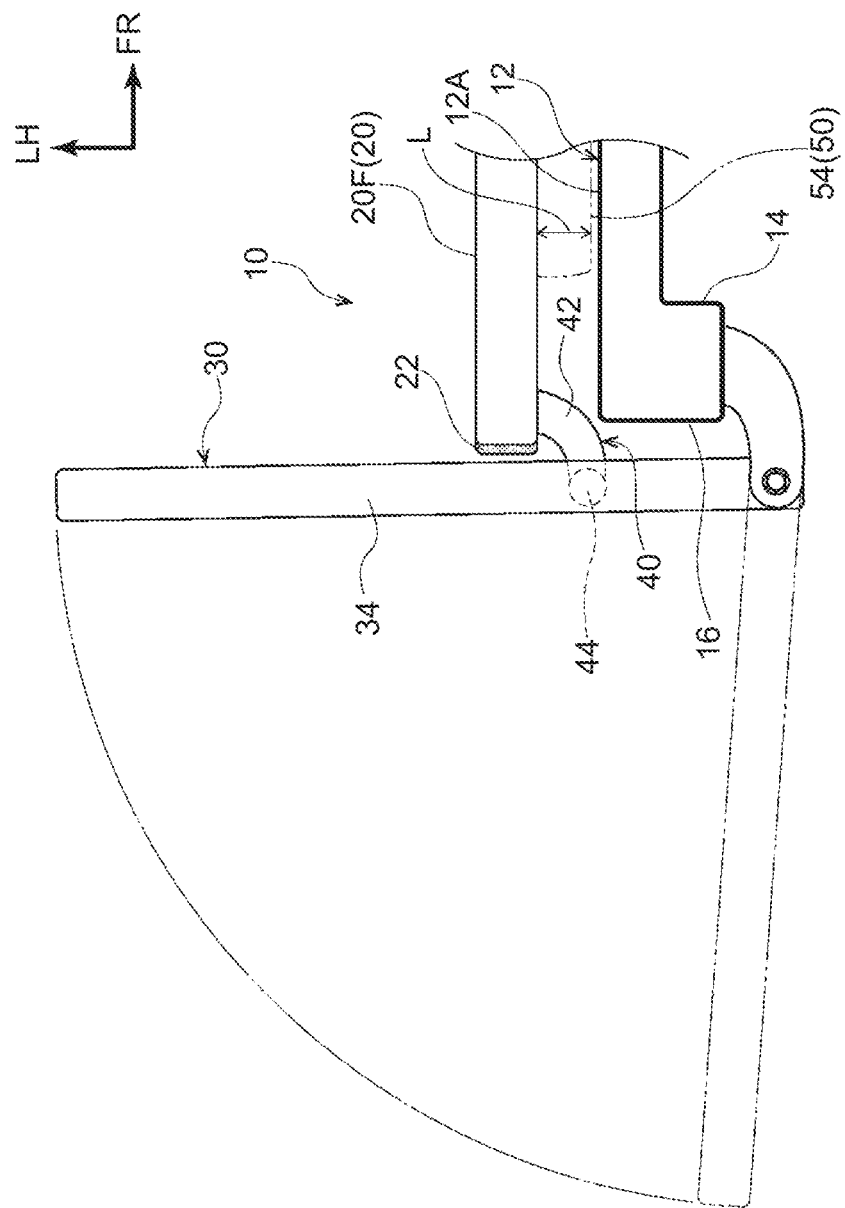
FIG. 8 is a plan view showing the deployed posture of the boarding handrail according to the first embodiment.
Figure 9:
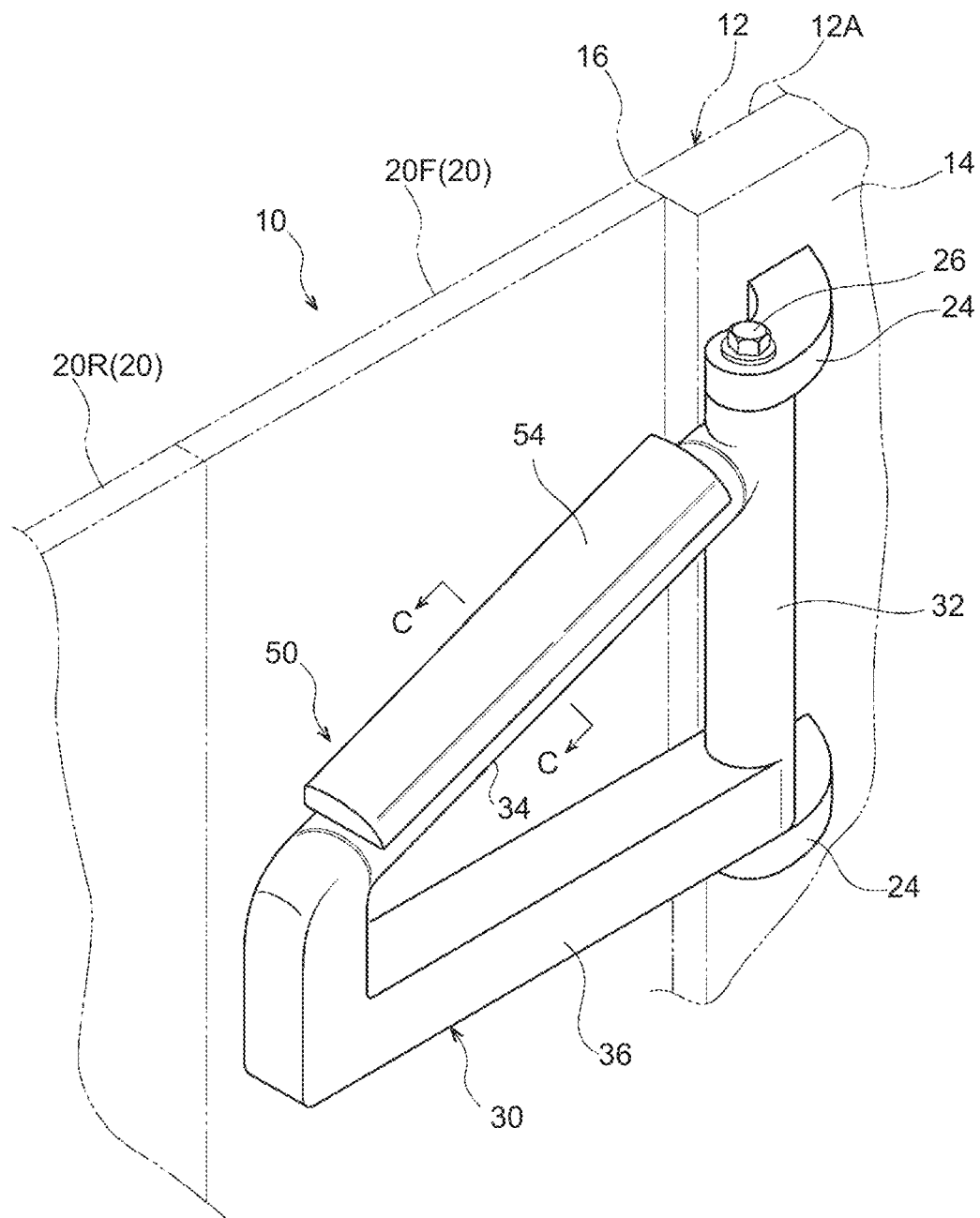
FIG. 9 is a perspective view showing the boarding handrail disinfecting device according to the first embodiment as seen from a vehicle cabin side.
Figure 10:
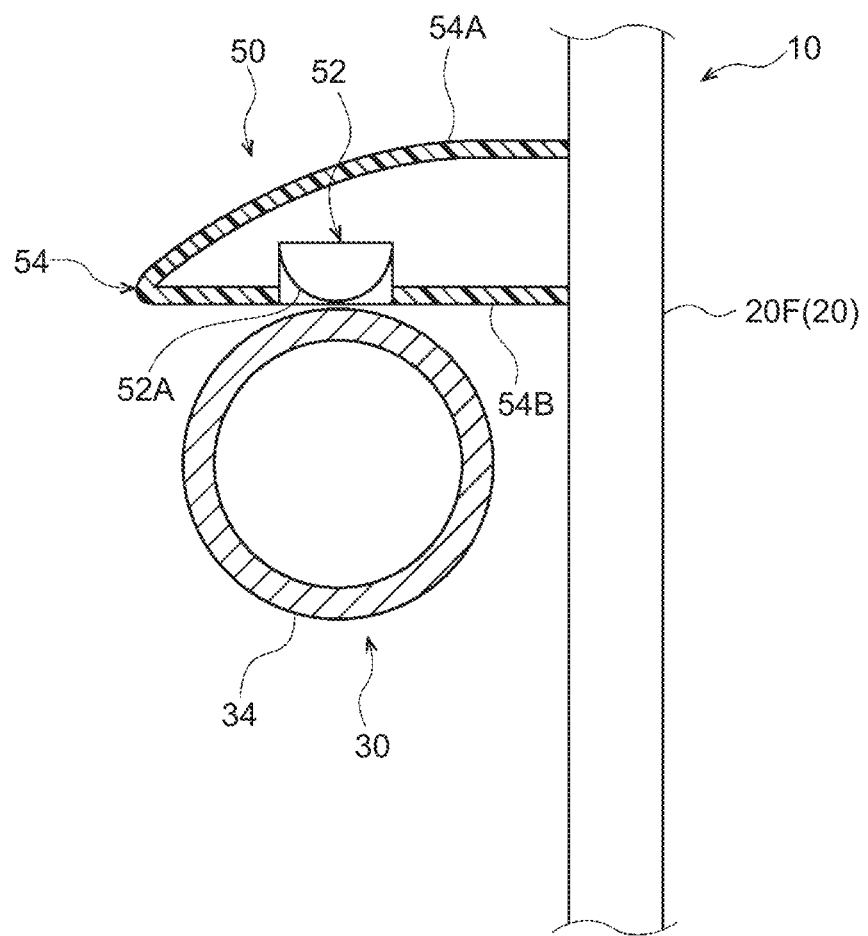
FIG. 10 is a sectional view taken along line C-C of FIG. 9 and seen in the arrow direction.

As shown in FIG. 8, a length L of the cover member 54 in a protruding direction in which it protrudes from the inner wall surface of the door half 20F (the length of protrusion along a thickness direction of the door half 20F) is such a length that when the door half 20F slides to open the entrance 16, the cover member 54 does not come into contact with the outer wall surface 12A of the vehicle body 12. As shown in FIG. 10, an upper surface 54A of the cover member 54 is formed as a curved surface having a substantially arc shape as seen in cross-section such that the thickness of the cover member 54 decreases as the cover member 54 extends in the protruding direction in which it protrudes from the inner wall surface of the door half 20F.

Figure 6:
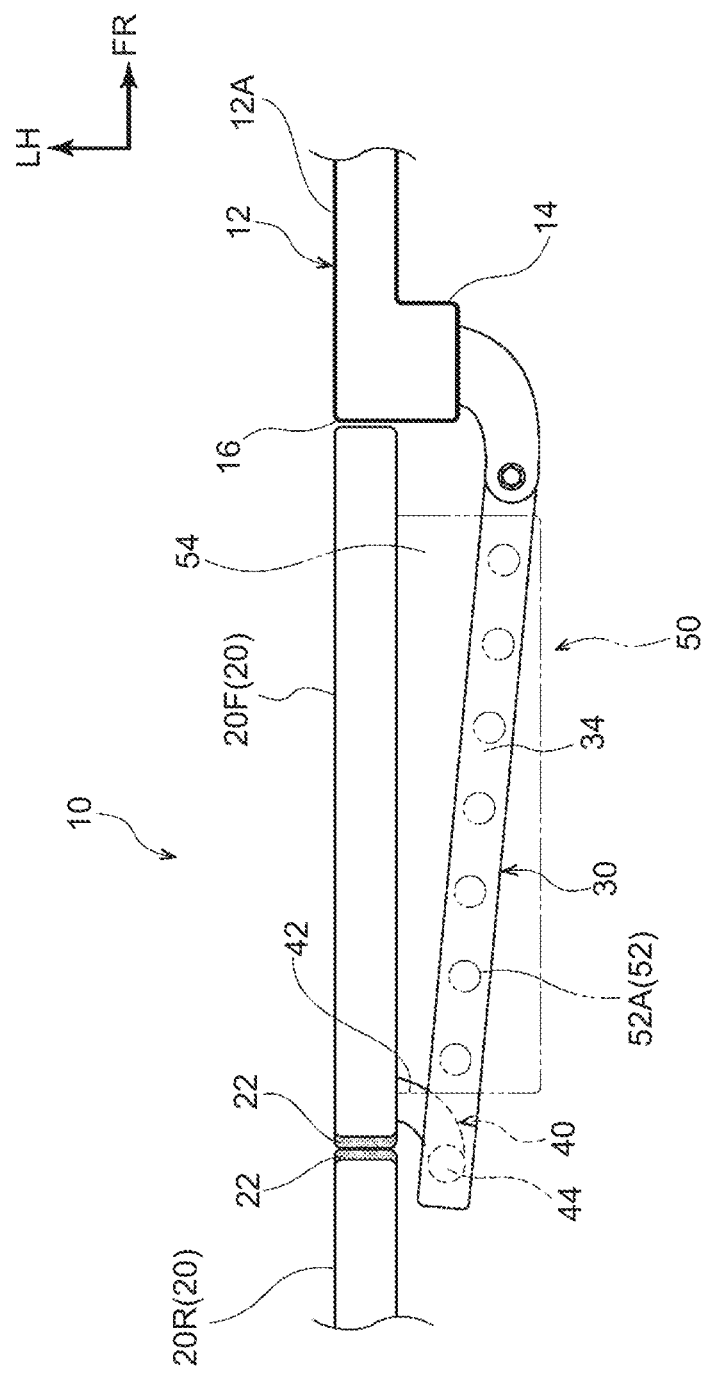
FIG. 6 is a plan view showing the retracted posture of the boarding handrail according to the first embodiment.

As shown in FIG. 6 and FIG. 10, an irradiation device 52 that irradiates the outer circumferential surface of the handrail main body 34 with ultraviolet light is provided at a predetermined position on a lower surface 54B of the cover member 54 that faces the handrail main body 34 in the up-down direction. The irradiation device 52 is compose of, for example, a plurality of ultraviolet light emitting elements (hereinafter referred to simply as "light emitting elements") 52A that is disposed along the longitudinal direction of the cover member 54. The irradiation device 52 is configured to be able to irradiate the outer circumferential surface of the handrail main body 34 with ultraviolet light from above evenly in the axial direction.

The irradiation device 52 and the cover member 54 constitute the disinfecting device 50 according to the first embodiment. It is preferable that the upper surface 54A of the cover member 54 have a light-blocking property of blocking at least ultraviolet light to keep ultraviolet light from leaking toward the upper side. As shown in FIG. 6, when the handrail main body 34 having assumed the retracted posture is disposed so as to be inclined relatively to the inner wall surface of the door half 20F as seen in a plan view, it is preferable that the light emitting elements 52A be disposed along the inclination of the handrail main body 34 so as to be located directly above the handrail main body 34.

The light emitting elements 52A of the irradiation device 52 are supplied with electricity from a battery (not shown) installed in the bus 10 through a cable (not shown) that is routed so as to pass through the inside of the door half 20F and the inside of the cover member 54. Turning on and turning off the irradiation device 52 is controlled by a controller (not shown) that is provided in the bus 10.

Specifically, when the controller recognizes that the entrance 16 has been closed by the sliding door 20, the controller issues a signal for supplying electricity to the irradiation device 52 to turn on the light emitting elements 52A. When the controller recognizes that the entrance 16 is next opened by the sliding door 20, the controller issues a signal for stopping electricity supply to the irradiation device 52 to turn off the light emitting elements 52A.

The light emitting elements 52A of the irradiation device 52 may be turned off not when the entrance 16 is next opened by the sliding door 20 but when a predetermined time has elapsed with the entrance 16 closed by the sliding door 20.

Next, the workings of the disinfecting device 50 of the boarding handrail 30 according to the first embodiment configured as has been described above will be described. First, the workings of the boarding handrail 30 will be described, and then the workings of the disinfecting device 50 will be described.

Figure 5:
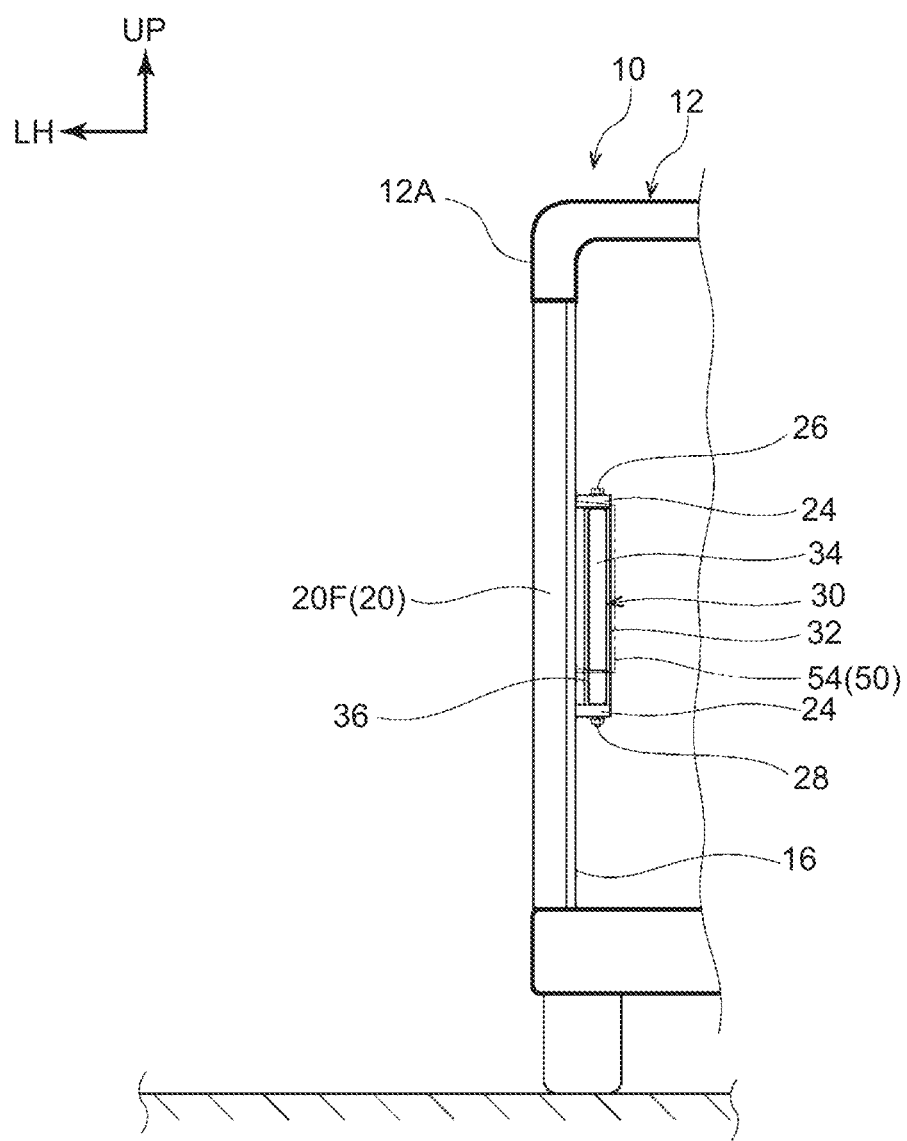
FIG. 5 is a rear view showing a retracted posture of the boarding handrail according to the first embodiment.

As shown in FIG. 5 and FIG. 6, when the entrance 16 is closed by the sliding door 20 (door halves 20F, 20R), the boarding handrail 30 is disposed almost along the sliding door 20 (the door half 20F in the case shown) as seen in a plan view. Specifically, when the entrance 16 is closed by the sliding door 20, the boarding handrail 30 assumes the retracted posture in which the sliding member 40 has slid toward the opposite side from the base 32 (toward the other end side) along the rail 36 and the handrail main body 34 and the rail 36 are disposed along the sliding door 20.

Thus, when the boarding handrail 30 assumes the retracted posture, the handrail main body 34 and the rail 36 do not protrude toward the inside of the vehicle (the vehicle cabin side). Therefore, especially in the small bus 10, when the boarding handrail 30 is provided, the boarding space is less restricted (as much boarding space as possible can be secured).

On the other hand, as shown in FIG. 7 and FIG. 8, when the entrance 16 is opened by the sliding door 20 (door halves 20F, 20R), the boarding handrail 30 protrudes toward the outside of the vehicle as seen in a plan view. Specifically, when the entrance 16 is opened by the sliding door 20, the boarding handrail 30 assumes the deployed posture in which the sliding member 40 has slid toward the base 32 along the rail 36 and the handrail main body 34 and the rail 36 protrude toward the outside of the vehicle (the outer side in the vehicle width direction).

Therefore, passengers can grasp the handrail main body 34 when getting on and off the bus 10 and thereby easily get on and off the bus 10 (with their posture stabilized). In particular, when getting off the bus 10, passengers momentarily stand on one foot while putting the other foot down. If the handrail main body 34 is present on the front side in their advancing direction, it helps passengers stand firmly on one foot and further stabilize their posture. Since the handrail main body 34 has a circular shape in cross-section, passengers can easily grasp the handrail main body 34 compared with when the handrail main body 34 has a rectangular shape in cross-section, for example.

Moreover, the handrail main body 34 extends from the upper part of the base 32 toward the obliquely lower side. In the case of the bus 10 provided with the slope 18 under the entrance 16, for example, the inclination angle θ1 of the slope 18 and the inclination angle θ2 of the handrail main body 34 can be set to nearly equal angles (so as to make the slope 18 and the handrail main body 34 substantially parallel to each other as seen in a rear view). Thus, when getting on and off the bus 10 using the slope 18, passengers can change the level of their fingers as the level of their body changes, which allows them to easily get on and off the bus 10 while grasping the handrail main body 34 (with their posture further stabilized).

When the boarding handrail 30 assumes the deployed posture, a clearance large enough to insert a finger is left between the handrail main body 34 and the elastic body 22 attached to the end surface of the door half 20F on the inner side in the front-rear direction. Therefore, even when a passenger inserts a finger between the handrail main body 34 and the elastic body 22 (touches the elastic body 22 with a finger) when getting on or off the bus 10 while grasping the handrail main body 34, that finger is unlikely to get hurt. Thus, the safety of passengers is secured.

When the sliding door 20 closes the entrance 16, the cover member 54 is disposed so as to closely face, from above, the handrail main body 34 of the boarding handrail 30 having assumed the retracted posture (see FIG. 10). When the controller recognizes that the entrance 16 has been closed by the sliding door 20, the controller performs control to turn on the light emitting elements 52A of the irradiation device 52 provided on the lower surface 54B of the cover member 54.

Thus, ultraviolet light is emitted from the irradiation device 52 to the outer circumferential surface of the handrail main body 34 evenly in the axial direction. As a result, the outer circumferential surface of the handrail main body 34 is sterilized (disinfected). Therefore, passengers who get on and off the bus 10 next can grasp the handrail main body 34 that has been sterilized. Thus, passengers who get on and off the bus 10 next can feel at ease about using the handrail main body 34.

In particular, since the cover member 54 is provided on the vehicle cabin side, passengers riding the bus 10 can see and learn that the handrail main body 34 is sterilized with ultraviolet light. Therefore, passengers riding the bus 10 can set their mind at ease about using the handrail main body 34. Thus, passengers riding the bus 10 can grasp the handrail main body 34 without hesitation, which can further enhance the safety of passengers during getting off the bus 10.

The cover member 54 is disposed so as to closely face the handrail main body 34 of the boarding handrail 30 only when the sliding door 20 closes the entrance 16 (only when the boarding handrail 30 assumes the retracted posture). In other words, the cover member 54 is withdrawn from the boarding handrail 30 when the entrance 16 is opened by the sliding door 20 (when the boarding handrail 30 assumes the deployed posture).

Therefore, passengers getting on and off the bus 10 can grasp the handrail main body 34 of the boarding handrail 30 from various directions, without the cover member 54 interfering with their action of grasping the handrail main body 34. Thus, the function of a boarding handrail 30 is not hindered despite the configuration in which the irradiation device 52 (disinfecting device 50) capable of emitting ultraviolet light to the handrail main body 34 of the boarding handrail 30 is provided.

When the controller recognizes that the entrance 16 is next opened by the sliding door 20 after the light emitting elements 52A of the irradiation device 52 are turned on, the controller performs control to turn off the light emitting elements 52A of the irradiation device 52. This configuration can reduce battery consumption compared with a configuration in which the light emitting elements 52A of the irradiation device 52 are kept in a turned-on state also when the entrance 16 is opened by the sliding door 20.

The boarding handrail 30 and the disinfecting device 50 (the cover member 54 having the irradiation device 52) thereof are not limited to the configuration in which they are provided only on the side of one door half (e.g., the door half 20F) of the sliding door 20. A configuration in which the boarding handrail 30 and the disinfecting device 50 thereof are provided on both sides of one door half (e.g., the door half 20F) and the other door half (e.g., the door half 20R) of the sliding door 20 may be adopted.

In this case, the boarding handrail 30 provided on the side of the door half 20R is disposed so as to be offset in the up-down direction from the boarding handrail 30 provided on the side of the door half 20F. This is because, due to the structure of the boarding handrail 30, the handrail main body 34 and the other end of the rail 36 provided on the side of the door half 20F protrude toward the door half 20R while the handrail main body 34 and the other end of the rail 36 provided on the side of the door half 20R protrude toward the door half 20F.

That the base 32, the handrail main body 34, and the rail 36 provided on the side of the door half 20R are thus offset in the up-down direction from the base 32, the handrail main body 34, and the rail 36 provided on the side of the door half 20F has an advantage in that passengers of various heights can select and grasp the handrail main body 34 that suits their own height. Of course, the sliding members 40 respectively mounted on the door halves 20F, 20R are also disposed so as to be offset from each other in the up-down direction according to the positions of the boarding handrails 30.

Second Embodiment

Next, a second embodiment will be described. Parts of the second embodiment that are equivalent to those of the first embodiment will be denoted by the same reference signs and a detailed description thereof will be omitted as appropriate.

Figure 11:
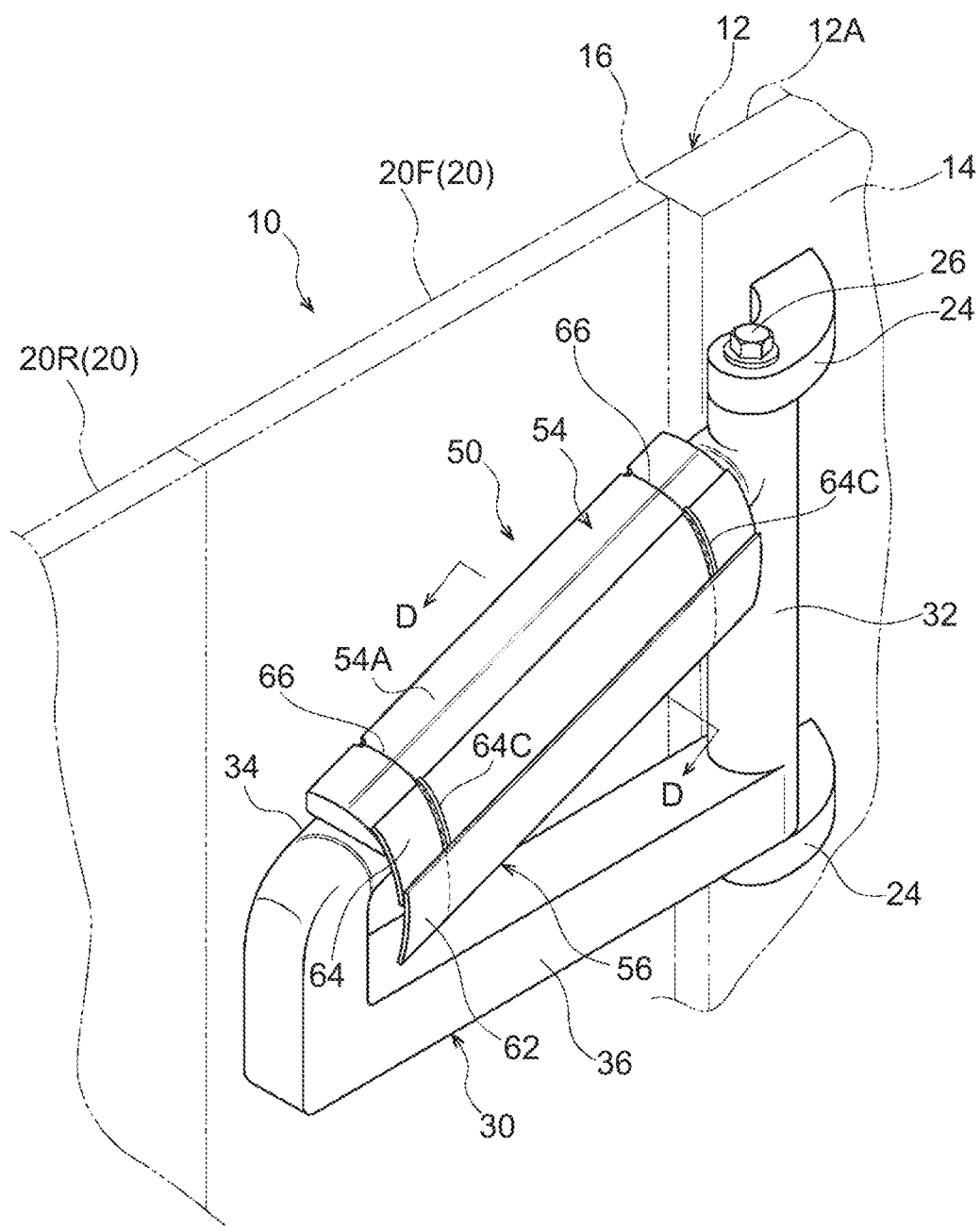
FIG. 11 is a perspective view showing a boarding handrail disinfecting device according to a second embodiment as seen from the vehicle cabin side.
Figure 12:
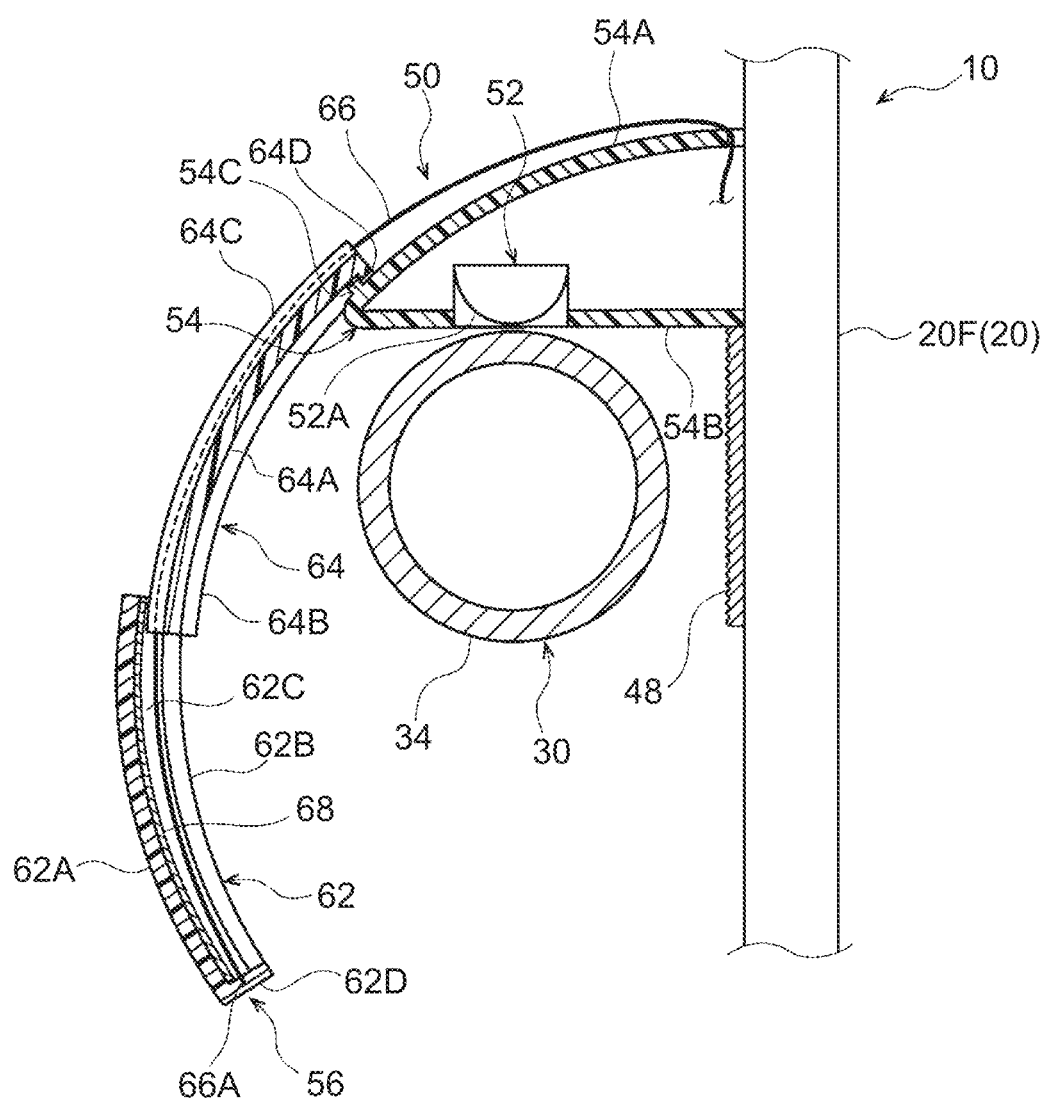
FIG. 12 is a sectional view taken along line D-D of FIG. 11 and seen in the arrow direction.
Figure 13:
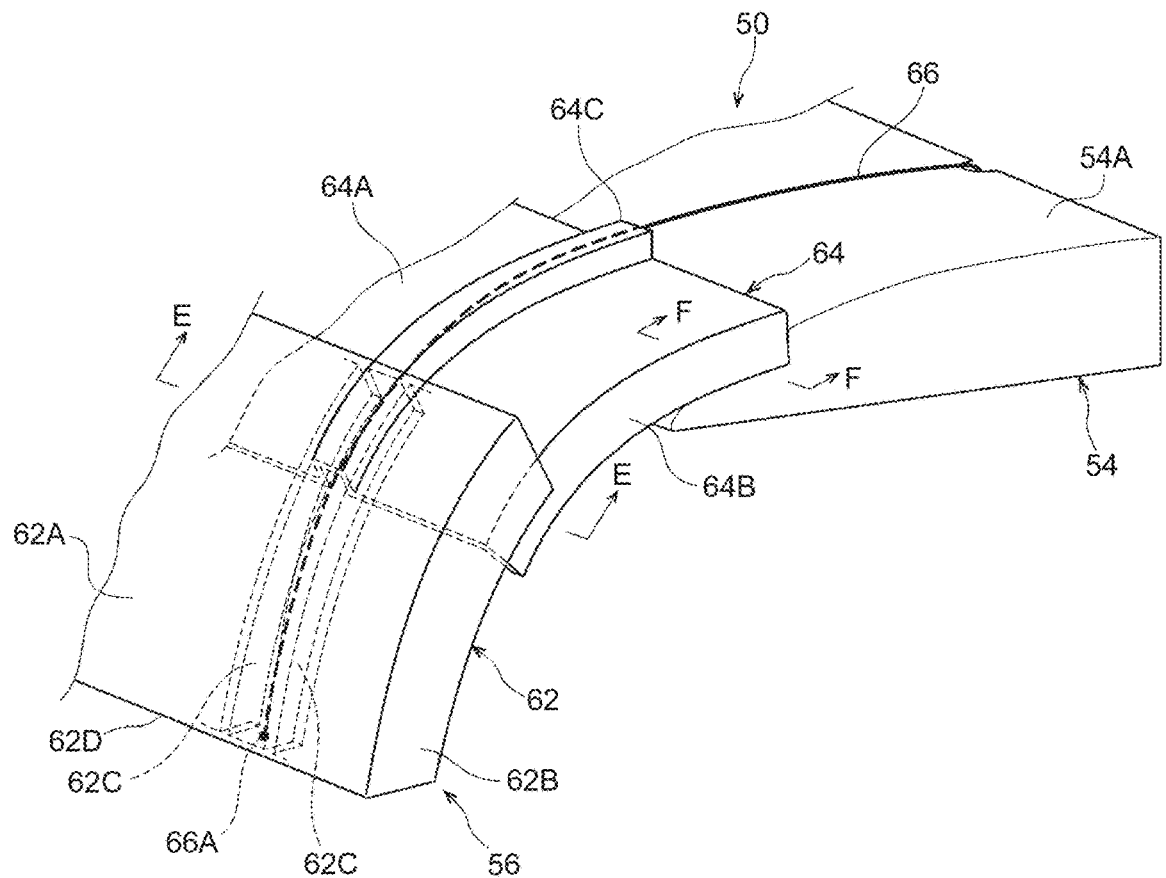
FIG. 13 is a perspective view showing a close-up of a part of a cover member of the boarding handrail disinfecting device according to the second embodiment.

As shown in FIG. 11 to FIG. 13, the disinfecting device 50 of the boarding handrail 30 according to the second embodiment differs from that according to the first embodiment in that the cover member 54 has an extending part 56 that extends (slides) downward and covers the handrail main body 34 of the boarding handrail 30 from the vehicle cabin side after the sliding door 20 (door half 20F) is closed.

The extending part 56 is composed of two sliding covers 62, 64 that have roughly the same shape as the cover member 54 as seen in a plan view, and the sliding covers 62, 64 are configured to be retractable onto the upper surface 54A of the cover member 54 in a state of lying one on top of the other. Hereinafter, a direction in which the sliding covers 62, 64 slide downward will be referred to as a deploying direction, and a direction in which the sliding covers 62, 64 slide upward will be referred to as a retracting direction.

Figure 14:
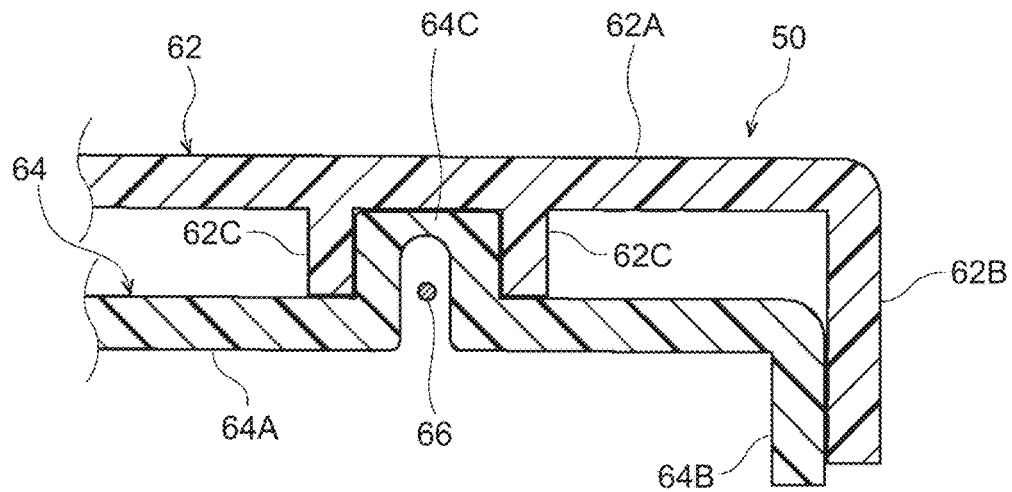
FIG. 14 is a sectional view taken along line E-E of FIG. 13 and seen in the arrow direction.

As shown in FIG. 12 to FIG. 14, the lower sliding cover 64 that is slidably laid on the upper surface MA of the cover member 54 has a main body 64A that has a curved plate shape in cross-section as seen from a longitudinal direction thereof, and side walls 64B that are integrally provided at both ends of the main body 64A in the longitudinal direction so as to extend downward. The sliding cover 64 has a substantially inverted U-shape in cross-section as seen from the deploying direction.

Near each end of the main body 64A of the sliding cover 64 in the longitudinal direction, a rectangular ridge 64C protruding upward is formed so as to bend along the deploying direction (retracting direction), and a wire 66 to be described later can be passed (housed) inside each of the ridges 64C.

Figure 15:
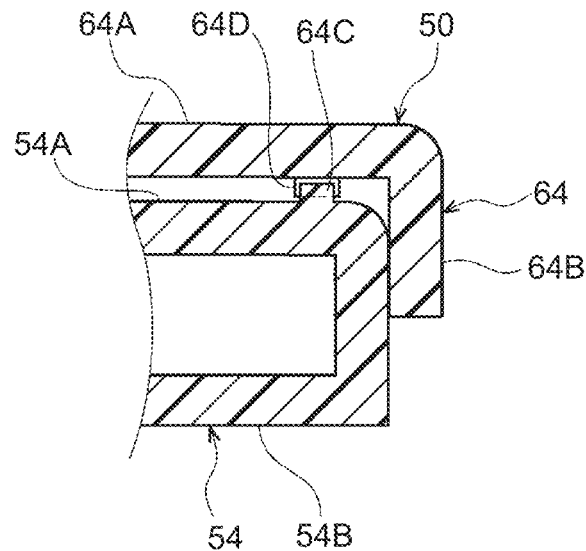
FIG. 15 is a sectional view taken along line F-F of FIG. 13 and seen in the arrow direction.

As shown in FIG. 12 and FIG. 15, a rectangular flat plate-shaped protrusion 64D protruding downward is integrally formed at an end of the main body 64A on a forward side in the retracting direction, near each end of the main body 64A in the longitudinal direction. A rectangular flat plate-shaped stopper 54C protruding upward is integrally formed at an end of the upper surface 54A of the cover member 54 on a forward side in the deploying direction, near each end of the upper surface 54A in the longitudinal direction (at a position corresponding to the protrusion 64D as seen from the deploying direction).

Thus, when the sliding cover 64 slides in the deploying direction, the protrusions 64D hit the stoppers 54C from the forward side in the retracting direction. This configuration limits the position of the sliding cover 64 to a predetermined position when the sliding cover 64 slides in the deploying direction.

On the other hand, as shown in FIG. 12 to FIG. 14, the upper sliding cover 62 that is slidably laid on an upper surface of the sliding cover 64 has a main body 62A that has a curved plate shape in cross-section as seen from a longitudinal direction thereof, and side walls 62B that are integrally provided at both ends of the main body 62A in the longitudinal direction so as to extend downward. The sliding cover 62 has a substantially inverted U-shape in cross-section as seen from the deploying direction.

The sliding cover 62 is formed a little larger than the sliding cover 64, and a pair of flat plate-shaped guide walls 62C protruding downward is integrally formed along the deploying direction (retracting direction) on an inner surface of the main body 62A, near each end thereof in the longitudinal direction. Each ridge 64C is inserted between the corresponding pair of guide walls 62C.

Thus, the interval between each pair of guide walls 62C is set to be equal to or slightly larger than the width of the ridge 64C. This configuration allows the sliding cover 62 to slide in the deploying direction and the retracting direction with the side walls 62B and the guide walls 62C thereof guided by the side walls 64B and the ridges 64C of the sliding cover 64.

Figure 16:
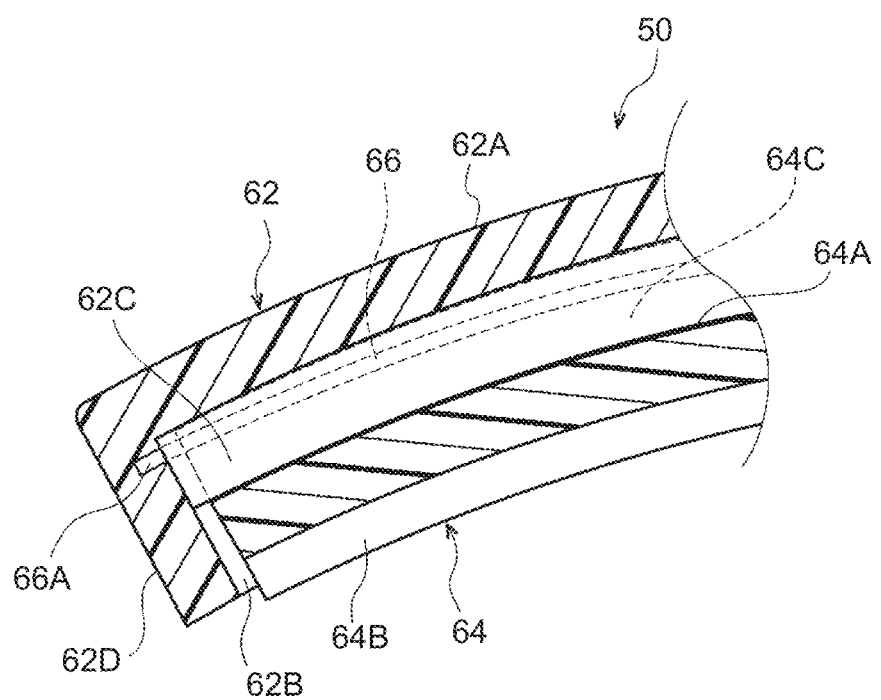
FIG. 16 is a sectional view showing a close-up of a part of the cover member of the boarding handrail disinfecting device according to the second embodiment.

As shown in FIG. 16, the sliding cover 62 has a front wall 62D that is integrally provided at an end of the main body 62A on the forward side in the deploying direction so as to extend downward (downward as seen in the retracted state).

One end portion 66A of each wire 66 passed through the inside of the ridge 64C is attached to an inner surface of the front wall 62D, near each end of the front wall 62D in the longitudinal direction.

Figure 17:
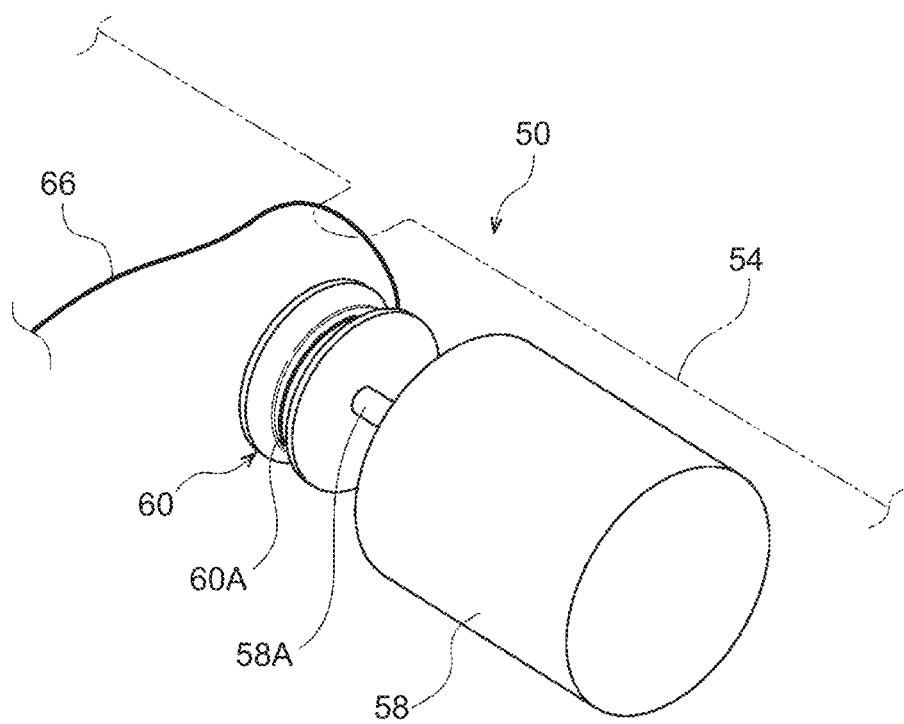
FIG. 17 is a perspective view showing a motor and a reeling member provided in the cover member of the boarding handrail disinfecting device according to the second embodiment.

As shown in FIG. 17, a motor 58 is provided at an end of the inside of the cover member 54 on the forward side in the retracting direction, near each end of the cover member 54 in the longitudinal direction, and a reeling member 60 that can reel the wire 66 is coaxially mounted on a rotating shaft 58A of each motor 58 that protrudes toward an inner side of the cover member 54 in the longitudinal direction. At a central portion of each reeling member 60 in an axial direction, a recessed groove 60A is formed continuously in a circumferential direction, and the other end portion (not shown) of the wire 66 is attached to a portion of the recessed groove 60A.

Here, when electricity is supplied from the battery installed in the bus 10 to the motors 58 through a cable (not shown), the reeling members 60 are driven to rotate synchronously by a rotation driving force of the motors 58 in a direction of reeling the wires 66. When electricity supply to the motors 58 is stopped, the reeling members 60 can rotate freely in a direction of unreeling the wires 66.

The length of each wire 66 is such a length that when the sliding cover 62 slides in the deploying direction, an end of the main body 62A on the forward side in the retracting direction is not separated from the end of the main body 64A of the sliding cover 64 on the forward side in the deploying direction (a state where these ends are laid one on top of the other is maintained) (see FIG. 12).

As shown in FIG. 12, a reflective plate 68 as a reflective member capable of reflecting ultraviolet light is integrally provided on an entire inner surface of the main body 62A of the sliding cover 62 (the surface facing the handrail main body 34). A reflective plate 48 as a reflective member capable of reflecting ultraviolet light and having a predetermined size (e.g., having a length nearly equal to that of the cover member 54 and a width nearly equal to the outside diameter of the handrail main body 34) is mounted parallel to the cover member 54 at a predetermined position in (on a part of) the inner wall surface of the door half 20F that closely faces the handrail main body 34 of the boarding handrail 30.

Next, the workings of the disinfecting device 50 of the boarding handrail 30 according to the second embodiment configured as has been described above will be described. The description of workings that are the same as workings of the disinfecting device 50 of the boarding handrail 30 according to the first embodiment will be omitted as appropriate.

When the sliding door 20 closes the entrance 16, the cover member 54 is disposed so as to closely face, from above, the handrail main body 34 of the boarding handrail 30 having assumed the retracted posture (see FIG. 11 and FIG. 12). When the controller recognizes that the entrance 16 has been closed by the sliding door 20, the controller performs control to stop electricity supply to the motors 58.

As a result, the reeling members 60 can rotate feely in the rotation direction in which the wires 66 are unreeled, so that the sliding covers 62, 64 slide in the deploying direction under their own weights. Here, the position of the upper sliding cover 62 in the deploying direction is limited by the wires 66. Meanwhile, the position of the lower sliding cover 64 in the deploying direction is limited as the protrusions 64D hit the stoppers 54C from the forward side in the retracting direction.

In this way, the handrail main body 34 is covered by the sliding covers 62, 64 (extending part 56) from the vehicle cabin side, with a predetermined clearance left therebetween. Then, the controller performs control to turn on the light emitting elements 52A of the irradiation device 52 provided on the lower surface 54B of the cover member 54. Thus, ultraviolet light is emitted from the irradiation device 52 to the outer circumferential surface of the handrail main body 34 evenly in the axial direction.

Here, the reflective plates 68, 48 are provided on the entire inner surface of the sliding cover 62 and on a part of the inner wall surface of the door half 20E Therefore, the ultraviolet light emitted from the irradiation device 52 is reflected by the reflective plates 68, 48, so that not only an upper surface side of the outer circumferential surface of the handrail main body 34 but also a lower surface side thereof etc. are irradiated with the ultraviolet light evenly in the axial direction (from various angles).

Thus, when the boarding handrail 30 (handrail main body 34) is not used, a disinfection treatment of the handrail main body 34 is intensively performed to entirely sterilize (disinfect) the outer circumferential surface of the handrail main body 34. Therefore, passengers who get on and off the bus 10 next can grasp the handrail main body 34 that has been sterilized. Thus, passengers who get on and off the bus 10 next can feel at ease about using the handrail main body 34.

Also the cover member 54 having the extending part 56 is disposed so as to closely face the handrail main body 34 of the boarding handrail 30 only when the sliding door 20 closes the entrance 16 (only when the boarding handrail 30 assumes the retracted posture). In other words, the cover member 54 having the extending part 56 is withdrawn from the boarding handrail 30 when the sliding door 20 opens the entrance 16 (when the boarding handrail 30 assumes the deployed posture).

Therefore, passengers getting on and off the bus 10 can grasp the handrail main body 34 of the boarding handrail 30 from various directions, without the cover member 54 having the extending part 56 interfering with their action of grasping the handrail main body 34. Thus, the function of a boarding handrail 30 is not hindered despite the configuration in which the irradiation device 52 (disinfecting device 50) capable of irradiating the handrail main body 34 of the boarding handrail 30 with ultraviolet light is provided.

When the controller recognizes that the entrance 16 is next opened by the sliding door 20 after the light emitting elements 52A of the irradiation device 52 are turned on, the controller performs control to turn off the light emitting elements 52A of the irradiation device 52 and supply electricity to the motors 58 to drive the reeling members 60 to rotate in the direction of reeling the wires 66.

Then, the sliding cover 62 slides in the retracting direction by being pulled by the wires 66, and the front wall 62D of the sliding cover 62 hits a front end of the sliding cover 64. By being pulled by the front wall 62D of the sliding cover 62, the sliding cover 64 slides in the retracting direction along with the sliding cover 62.

In this way, the sliding cover 62 and the sliding cover 64 are retracted onto the upper surface of the cover member 54. Therefore, when the entrance 16 is opened by the sliding door 20, the extending part 56 (sliding covers 62, 64) of the cover member 54 does not interfere with the opening action of the sliding door 20.

While the disinfecting devices 50 of the boarding handrail 30 according to the embodiments have been described above based on the drawings, the disinfecting devices 50 of the boarding handrail 30 according to the embodiments are not limited to those shown in the drawings, and design changes can be made thereto as necessary within the scope of the gist of the present disclosure. For example, in the first embodiment, as in the second embodiment, the reflective plate 48 capable of reflecting ultraviolet light may be mounted at a predetermined position in (on a part of) the inner wall surface of the door half 20F.

In the second embodiment, a configuration in which a reflective plate (not shown) is provided also on the lower surface 54B of the cover member 54 may be adopted. Further, a configuration in which a reflective plate (not shown) is provided also on an entire inner surface of the lower sliding cover 64 may be adopted. The irradiation device 52 is not limited to a device composed of a plurality of light emitting elements 52A, and may have any configuration as long as the irradiation device 52 can emit ultraviolet light.

Turning on of the light emitting elements 52A is not limited to the configuration in which it is triggered by the controller's recognizing that the sliding door 20 has closed. For example, a configuration in which turning on of the light emitting elements 52A is triggered by operation of a switch for closing the sliding door 20 performed by a driver of the bus 10 may be adopted. However, the configuration in which turning on of the light emitting elements 52A is triggered by the controller's recognizing that the sliding door 20 has closed can be applied to a self-driving bus on which no driver is present.

In the second embodiment, instead of the configuration in which the motors 58 are provided for the respective wires 66, the rotating shaft 58A of a single motor 58 may be protruded from both sides in an axial direction and the reeling members 60 may be mounted on the rotating shaft 58A. Thus, a configuration in which the reeling members 60 that reel the wires 66 are driven to rotate by a single motor 58 may be adopted. Further, the disinfecting device 50 may be provided on a boarding handrail (not shown) that is fixed inside a vehicle, for example, as long as the configuration does not interfere with an action of grasping this boarding handrail.

A protective member (not shown) that is molded from a fiber material or a rubber material having water-repellent and antibacterial properties, for example, may be wrapped around the handrail main body 34. In this case, this protective member should be irradiated with ultraviolet light. The power source for the irradiation device 52 is not limited to the battery installed in the bus 10. For example, a battery holder (not shown) may be provided inside the cover member 54 and a plurality of dry-cell batteries (not shown) housed in this battery holder may be used as the power source.

What is claimed is:

1. A boarding handrail disinfecting device comprising:
   a cover member that is provided on a door for opening and closing an entrance of a vehicle, and that is disposed so as to closely face a boarding handrail provided on a periphery of the entrance when the door closes the entrance and withdrawn from the boarding handrail when the door opens the entrance; and
   an irradiation device that is provided on a surface of the cover member that faces the boarding handrail and irradiates the boarding handrail with ultraviolet light.

2. The boarding handrail disinfecting device according to claim 1, wherein the cover member has an extending part that extends and covers the boarding handrail after the door is closed.

3. The boarding handrail disinfecting device according to claim 2, wherein a reflective member capable of reflecting ultraviolet light is provided on a surface of the extending part that faces the boarding handrail.

4. The boarding handrail disinfecting device according to claim 1, wherein a reflective member capable of reflecting ultraviolet light is provided on a part of the door that closely faces the boarding handrail when the door closes the entrance.

* * * * *